United States Patent [19]
Kurer

[11] Patent Number: 5,118,294
[45] Date of Patent: Jun. 2, 1992

[54] DENTAL CROWN PREPARATION METHOD

[76] Inventor: Hans G. Kurer, 6 Blenheim Close, Hale, Altrincham, Cheshire WA15 2RU, England

[21] Appl. No.: 632,104

[22] Filed: Dec. 20, 1990

[30] Foreign Application Priority Data

Apr. 17, 1990 [GB] United Kingdom ............... 9008515

[51] Int. Cl.⁵ .......................... A61C 5/08; A61C 8/00; A61C 5/00
[52] U.S. Cl. ................................ 433/220; 433/174; 433/215
[58] Field of Search ............ 433/218, 219, 220, 221, 433/174; 433/75, 76

[56] References Cited

U.S. PATENT DOCUMENTS

| 3,524,255 | 8/1970 | Kurer | 32/13 |
| 4,738,616 | 4/1988 | Reynauld | 433/220 |
| 4,787,848 | 11/1988 | Ross | 433/165 |

FOREIGN PATENT DOCUMENTS 721042  2/1932  France ............... 433/220

Primary Examiner—John G. Weiss
Assistant Examiner—Cindy A. Cherichetti
Attorney, Agent, or Firm—Bell, Seltzer, Park & Gibson

[57] ABSTRACT

A method of accurately positioning a post in a tooth root to receive a tooth crown is proposed wherein a stepped bore having successive sections is formed in the tooth root in accurate axial alignment one with the other by locating a jig in a first bore part and utilizing that jig in the precision drilling of the second bore part.

5 Claims, 2 Drawing Sheets

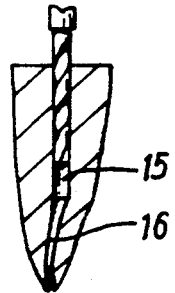
Fig. 6a Preliminary drilling
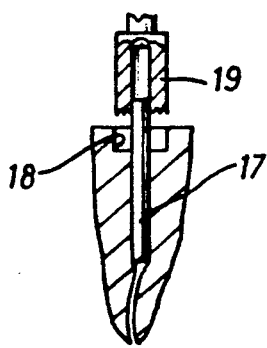
Fig. 6b Counterbore
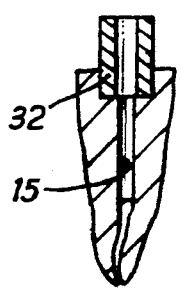
Fig. 6c Fit sleeve
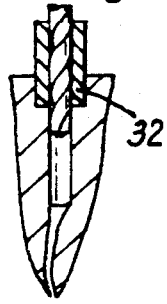
Fig. 6d Precision drilling
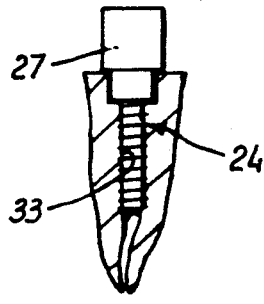
Fig. 6e Locate headed post
Fig. 6f Grind head to shape
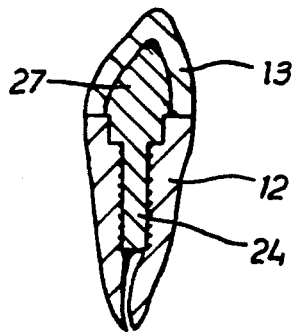
Fig. 6g Fit crown

DENTAL CROWN PREPARATION METHOD

The invention concerns improvements in or relating to dentistry, and has more particular reference to the attachment of tooth crowns to a tooth root.

In the art of tooth restoration it is common practice to secure a tooth crown to an existing tooth root by locating a threaded post in a drilled and tapped hole formed in a tooth root canal and applying the crown to a shaped head to that post, such practice being described, for example, in British Patent specification No. 1092982.

Whilst the practice aforesaid did, at the time, represent a significant advance over the then conventional methods, and indeed has, in the meantime, become a standard procedure for tooth restoration, a shortcoming in the method by which the post is located in the tooth root has been recognized. More particularly, whilst in the vast majority of cases the attachment of the crown is secure and remains so almost indefinitely, in some instances the post does become loosened, and some remedial action is required.

The object of the present invention is to provide a method for the attachment of a tooth crown which avoids the shortcoming of the method heretofore practiced as regards long term security of the post in the tooth root.

According to its broadest aspect the invention proposes a method for the in situ preparation of a tooth root to provide a stepped blind hole to receive a crow post into engagement therewith, the stepped blind hole having inner and outer sections of respective axial and radial dimensions, the method including the steps of drilling said tooth root canal to provide a blind hole approximating to the radial dimensions of one of the inner and outer sections and to the axial dimension thereof measured from the tooth root face, locating a jig in the thus formed hole to provide a guide, and drilling said blind hole to conform to the axial and radial dimensions of the other of the said sections using said jig as a guide, thereby to ensure accurate axial alignment between the inner and outer sections.

The drilling of the first and second sections may be effected simultaneously by means of a complex drill each respective part acting as a guide for the other part as the drilling progresses. The drill may include a facility for adjustment as to length of the inner section of the blind hole.

In practicing the invention a preferred method for the attachment of a tooth crown to a tooth root comprising the steps of drilling the tooth root to form a blind hole therein, providing a counterbore at the root face in register with the blind hole, locating a post in said blind hole and in engagement with said counter-bore, and applying a tooth crown to the post is characterized in that, in providing the counterbore, a support means is located in axial alignment with the blind hole to extend therefrom and said support means is utilized as a guide in drilling the counterbore in accurate axial alignment with the blind hole.

The support means will comprise a dummy post engageable with the blind hole in the tooth root and the counterbore is formed by an annular face-drill arranged coaxially with and slidable on the dummy post into engagement with the tooth root face.

Preferably, the method includes the further steps of locating a sleeve-like jig in closely fitting relationship with the counterbore, redrilling the tooth root canal to a requisite depth and diameter, utilizing the jig as a guide, and removing the sleeve-like jig on completion of the drilling to leave a stepped bore to receive a stepped crown post into engagement therewith.

The invention will now be described further, by way of example only, with reference to the accompanying diagrammatic drawings illustrating one embodiment thereof and in which:

FIG. 6 is a schematic illustration of the successive stages of a modified procedure in accordance with the invention.

Figure 1:
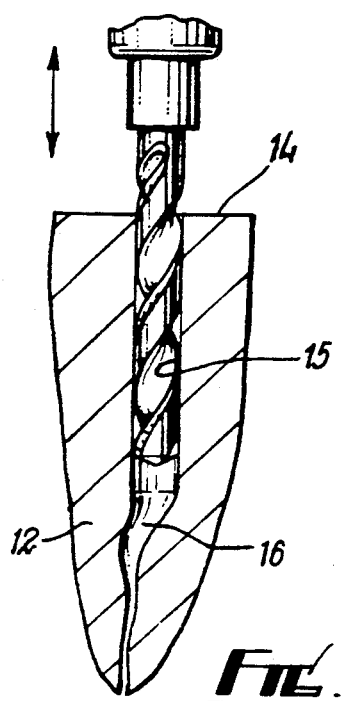
FIG. 1 illustrates the forming of a blind hole in the tooth root.

Research into the security of attachment of a tooth crown fitted in accordance with the known post system has led to the finding that failure of that attachment is related to lateral, rather than axial, forces applied to the crown and has been identified with the absence of an accurate coaxial relationship between the blind hole drilled in the tooth root and the counterbore formed in the tooth root face and which is intended to receive the head of the crown post into engagement therewith. It is believed that a cantilever effect occurs in the presence of lateral loads which, in the absence of an accurate coaxial relationship as aforesaid, is not adequately supported.

By ensuring accurate axial alignment between the blind hole and counterbore, as is possible by the method of the invention, adequate support is provided to sustain the lateral loads, and it is believed that the incidence of failure will be much reduced or, at best, eliminated.

Referring now to the drawings, and particularly to FIGS. 1 to 4 thereof, in positioning a crown post 11 in a tooth root 12 to receive a tooth crown 13, the root face 14 is prepared and a blind hole 15 is drilled in the tooth root canal 16, the blind hole 15 then being threaded or not as desired. Typically, the blind hole will be between 0.75 to 2.5 mm in diameter and between 5 and 12 mm deep.

In accordance with the invention a cylindrical dummy post 17 (FIG. 2) is engaged with the blind hole 15, the post being dimensioned so as to be a close and secure fit in the blind hole and so as to extend outwardly therefrom. A counterbore 18 is cut in accurate co-axial relationship with the blind hole using a sleeve drill 19 having an annular cutting face 20 at the lower end 21 thereof, the bore 22 of the sleeve drill 19 being a close clearance on the upper end 23 of the dummy post 17 and such drill 19 being guided on such post 17 in its movement towards and into contact with the root face 14. Typically the counterbore will be between 1 and 3 mm in diameter and from 0.5 to 4 mm in depth.

After having drilled the counterbore 18 to a sufficient depth, the dummy post is removed and a stepped crown post 24 is screwed into or placed in the blind hole 15 (FIG. 3), the transverse dimension of the second tier section 25 of the crown post 24 corresponding to the diameter of the counterbore 18 and seating therein.

As will be appreciated, dental cement, not shown, will be applied between the crown post 24 and the blind hole/counterbore 15, 18 and provision will ordinarily be made for the removal of excess cement and for the release of air from the tooth root, as by the inclusion of a venting groove 26, in accordance with conventional dental practice.

The head 27 of the crown post is ground in situ to a requisite shape (FIG. 4), and the tooth crown 13 is prepared by reference to a dental impression of the post and of the surrounding teeth in accordance with conventional practice. The restoration is completed by fitting the crown to the shaped head of the post.

Figure 5:
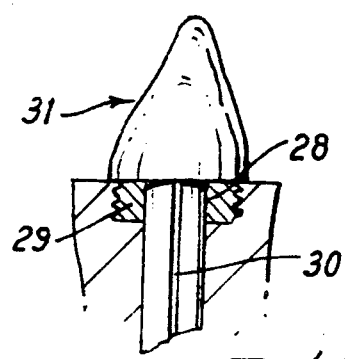
FIG. 5 is a view corresponding to FIG. 3, and shows the use of a sleeve in the counterbore to receive a crown post.

Whilst it is proposed to utilize a stepped post of the character of that shown in the drawings, it may be found convenient, in some circumstances, to utilize a separate collar 28 (see now FIG. 5) for engagement with the counterbore 29, the outer surface of such collar being threaded for secure engagement with the counterbore and the inner surface thereof being a close clearance on the stem 30 of the crown post 31, the post, in this instance, being plane, although a threaded post may be used if desired.

Figure 2:
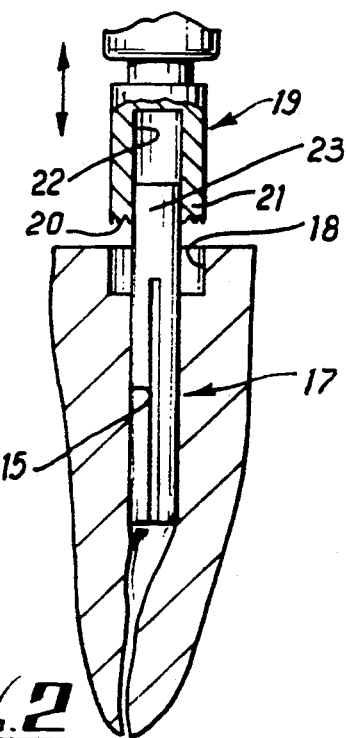
FIG. 2 illustrates the location of a dummy post in the blind hole and the drilling of a counterbore in accurate coaxial relationship to the blind hole.
Figure 3:
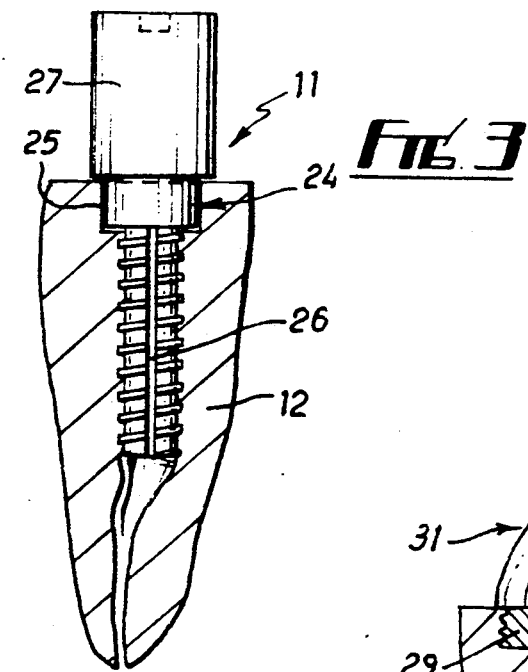
FIG. 3 shows a stepped post engaged with the blind hole and counterbore.
Figure 4:
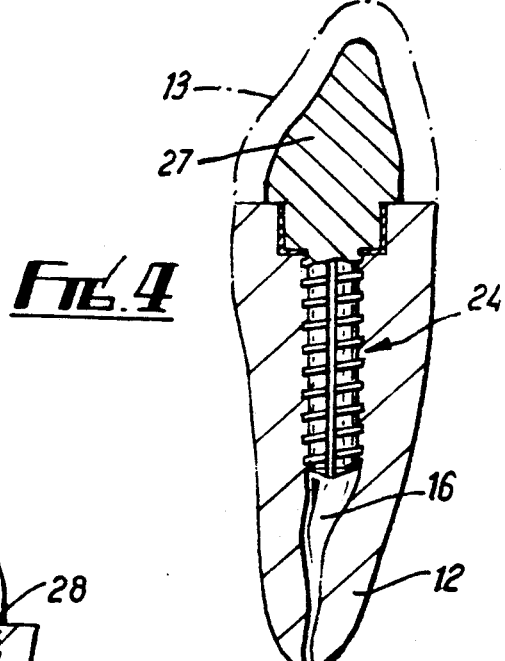
FIG. 4 illustrates the in situ grinding of the head of the post to a form suitable to receive a tooth crown.

In a modification of the procedure outlined with reference to FIGS. 1 to 4, after having cut counterbore 18 by means of annular face drill 19 in the manner illustrated by FIG. 2, a sleeve 32 is located in closely fitting relationship therewith and such sleeve is utilized as a jig in the precision drilling of the tooth root canal 16. In this procedure dummy post 17 will not ordinarily be threaded, and blind hole 15 will be after the nature of a "preliminary" drilled hole for the primary purpose of accurately forming counterbore 18 which, in turn, provides a basis for the precision drilling of a bore 33 to receive a headed post 24 or its equivalent. Use of the sleeve 32 as a guide for the precision drilling of the tooth root canal ensures accurate axial alignment of the sleeve 32 and headed post 24 and the secure attachment of such post 24 with respect to the tooth root 12.

If the sleeve is to be used merely as a guide in the precision drilling of the inner bore, as distinct from remaining in the counterbore as a part of the tooth restoration, it may be found convenient to utilize a post of significantly greater axial dimension than the corresponding dimension of the counterbore, a length of 4 to 5 mms being thought to be appropriate. The provision of an external screw thread to the sleeve would ensure accuracy of location thereof for the subsequent drilling step, the guidance offered by the dummy post facilitating proper location thereof in the counterbore in the event that the thread is of the self-tapping variety.

The sequence of steps of the modified procedure is shown diagrammatically in FIG. 6, the successive stages shown therein being as follows:

a. Preliminary drilling of tooth root canal 16;
b. Fit dummy post 17 and drill counterbore 18 utilizing post as jig;
c. Fit sleeve 32 into counterbore 18, the sleeve to have internal/external threads if desired, with any necessary threading of counterbore;
d. Precision drilling of tooth root canal, using sleeve 32 as a jig;
e. Create thread in precision drilled bore 33, if desired, and locate headed post 24 therein;
f. Grind post head 27 to shape; and
g. Fit tooth crown 13.

The invention is not limited to the detail of the embodiment herein set forth, and alternatives will readily present themselves to one skilled in the art. It will be appreciated that a like effect can be attained by use of a complex drill having a lead section whereby the blind hole in the root canal might be formed and an annular cutting surface to form the counterbore, the blind hole and counterbore being formed in sequence with the requisite accurate coaxial relationship therebetween, the lead section of the drill providing the requisite support to the drill during formation of the counterbore, thus to maintain such coaxial relationship. Furthermore, whilst reference is made herein to the use of a headed post which is subsequently ground, in situ, to a requisite shape, it may be preferred, in some instances, to add a core to a post, the fixed core illustrated representing merely one way of creating a structure to receive the crown.

It has been found that, by adopting the method herein proposed, the problem inherent in the prior art, for example the poor fit of prefabricated parts particularly at the coronal end of the post space arising from a non-circular entrance to the bore as a result of hand held enlargement, is avoided, and proper coaxial relation between the inner and outer sections of the bore is assured.

I claim:

1. A method for the in situ preparation of a tooth root to provide a stepped blind hole to receive a crown post into engagement therewith, the stepped blind hole having inner and outer sections of respective axial and radial dimensions, the method including the steps of drilling said tooth root canal to provide a blind hole approximating to the radial dimension of the outer section and to the axial dimension thereof measured from the tooth root face, locating a sleeve in the thus formed hole to provide a guide, and precision drilling the inner section of said blind hole to conform to the required axial and radial dimensions thereof using said sleeve as a guide, thereby to ensure accurate axial alignment between the inner and outer sections.

2. A method as claimed in claim 1, including the preliminary steps of forming a blind bore in the tooth root to a transverse dimension approximating to the diameter of the intended inner section thereof, locating a post in said blind bore in closely fitting relationship thereto to define a jig extending outwardly from the tooth root face for use in drilling the said blind hole in conformity with the radial and axial dimensions of the outer section.

3. A method for the attachment of a tooth crown to a tooth root comprising the steps of drilling the tooth root to form a blind hole therein, provided a counterbore at the root face in register with the blind hole, locating a post in said blind hole and in engagement with said counterbore, and applying a tooth crown to the post characterized in that, in providing the counterbore, a support means is located in axial alignment with the blind hole to extend therefrom and said support means is utilized as a guide in drilling the counterbore in accurate axial alignment with the blind hole, removing the support means from the blind hole, securing a sleeve in the counterbore in closely fitting relationship thereto, and utilizing the sleeve as a jig in the precision re-drilling of the blind hole at that part thereof inwardly of the sleeve with respect to the tooth root face in accurate axial alignment with the sleeve.

4. A method for the in situ preparation of a tooth root having a tooth root canal and a tooth root face to provide a stepped blind hole to receive a crown post into engagement therewith, the stepped blind bore having an inner section and an outer section of respective axial and radial dimensions, the method including the steps of drilling the tooth root canal to provide a blind hole approximating to the radial dimension of the said inner section and to the axial dimension thereof as measured from the tooth root face, locating a dummy post in the thus formed hole to provide a guide, the dummy post extending outwardly beyond the said tooth root face, and drilling the tooth root face with a sleeve drill having an inner diameter approximating the diameter of said inner section and an outer diameter corresponding to the diameter of said outer section, to form an annular counterbore axial with the inner section of the blind bore, removing the dummy post, locating a sleeve in closely fitting relationship with the outer section of the stepped blind bore, the sleeve having an inner diameter corresponding to the intended radial dimension of said inner section, and precision drilling said inner section using the sleeve as a guide.

5. The method as claimed in claim 4, including the further steps of removing the sleeve and securing in the blind bore a post having sections complementarily dimensioned with regard to and in closely fitting relationship with respective ones of the inner and outer sections of said bore.

* * * * *